United States Patent
Hong et al.

(10) Patent No.: US 9,227,904 B1
(45) Date of Patent: Jan. 5, 2016

(54) METHOD FOR PRODUCING GLUCARIC ACID

(71) Applicants: HYUNDAI MOTOR COMPANY, Seoul (KR); SNU R&DB FOUNDATION, Seoul (KR)

(72) Inventors: Chae Hwan Hong, Seoul (KR); Si Hwan Kim, Anyang-si (KR); Young Gyu Kim, Gunpo-si (KR); Na Ra Shin, Seoul (KR)

(73) Assignees: HYUNDAI MOTOR COMPANY, Seoul (KR); SNU R&DB FOUNDATION, Seoul (KR)

( * ) Notice: Subject to any disclaimer, the term of this patent is extended or adjusted under 35 U.S.C. 154(b) by 0 days.

(21) Appl. No.: 14/565,175

(22) Filed: Dec. 9, 2014

(30) Foreign Application Priority Data

Aug. 18, 2014 (KR) .................. 10-2014-0107114

(51) Int. Cl.
| | | |
|---|---|---|
| *C07C 51/295* | (2006.01) | |
| *C07C 55/12* | (2006.01) | |
| *C07C 51/31* | (2006.01) | |

(52) U.S. Cl.
CPC ............ *C07C 51/313* (2013.01); *C07C 55/12* (2013.01)

(58) Field of Classification Search
None
See application file for complete search history.

(56) References Cited

U.S. PATENT DOCUMENTS

| | | | |
|---|---|---|---|
| 2,472,168 A | * | 6/1949 | Mehltretter et al. .......... 562/531 |
| 4,876,195 A | | 10/1989 | Shirafuji et al. |
| 2010/0317823 A1 | | 12/2010 | Boussie et al. |
| 2014/0256982 A1 | | 9/2014 | Boussie et al. |

FOREIGN PATENT DOCUMENTS

| | | |
|---|---|---|
| KR | 95-0005132 B1 | 5/1995 |
| KR | 2013-0012426 A | 2/2013 |
| WO | 2011-155964 A1 | 12/2011 |
| WO | 2013-183610 A1 | 12/2013 |

OTHER PUBLICATIONS

Moon, Tae Seok, et al.,: "Production of Glucaric Acid from a Synthetic Pathway in Recombinant *Escherichia coli*", Applied and Environmental Microbiology, Feb. 2009, vol. 75, No. 3, pp. 589-595.

* cited by examiner

*Primary Examiner* — Yevegeny Valenrod
(74) *Attorney, Agent, or Firm* — McDermott Will & Emery LLP

(57) ABSTRACT

The present disclosure relates to a method for producing glucaric acid, and more particularly, to a method for producing glucaric acid including the steps of: (1) inputting aldohexose and potassium hydroxide to an aqueous solution; and (2) deriving a catalytic oxidation reaction after adding a supported noble metal catalyst to the aqueous solution under the presence of oxygen gas.

8 Claims, 9 Drawing Sheets

METHOD FOR PRODUCING GLUCARIC ACID

CROSS-REFERENCE TO RELATED APPLICATION

This application is based on and claims priority from Korean Patent Application No. 10-2014-0107114, filed on Aug. 18, 2014 in the Korean Intellectual Property Office, the entire disclosure of which is hereby incorporated by reference herein.

BACKGROUND OF THE DISCLOSURE

1. Field of the Disclosure

The present disclosure relates to a method for synthesizing glucaric acid, which can be used as a raw material for adipic acid, from aldohexose obtained from plants or marine resources.

2. Description of the Prior Art

Due to continuous increase in population and development of industry, oil resources are the resources mankind is most dependent to the extent that it occupies 95% of the currently produced chemicals. However, the limitation of oil deposits and the inevitable environmental problems caused by extracting such deposits, it is urgent to establish an alternative.

Hence, recently, various alternative materials capable of replacing oil resources are actively studied, and above all, since biomass which is derived from plant resources repeatedly produced annually in nature such as corn, sugar cane, wood-based plant resources, palm, algae, etc. is eco-friendly as well as reproducible, it has emerged as an important future resource.

However, the bio material business is still a small business, and also the economy is lower than petrochemical materials. But, according to the report by EPNOE (European Polysaccharide Network of Excellence) and announced by Utretch University of Netherlands, it predicts that the usage of biomass is rapidly increased after 10 years and concretely, it is marketable to the extent that it can replace 90% of oil-extracting materials.

On the other hand, the industrial importance of the biomass related study has been increasingly emphasized in terms of automotive component materials deeply associated with oil resources. For example, polypropylene, nylon, polycarbonate, and ABS materials, etc. are used as an interior and exterior injection molding material, polypropylene material of them is most widely used in quantity, followed by nylon material (around about 15 kg per vehicle). In particular, because Nylon 66 of the nylon materials has excellent physical properties such as heat resistance, wear resistance, and chemical resistance, etc., it is widely used as the component requiring high temperature characteristics of automotive components next to Nylon 6.

Nylon 66 is prepared by dehydration polymerization of hexamethylenediamine and adipic acid. The adipic acid monomer has been produced by chemical synthesis process in which cyclohexane is obtained from crude oil refinement process, starting from crude oil, as an intermediate (e.g., crude oil→benzene→cyclohexane→adipic acid→Nylon 66). However, the above described technology and process of manufacturing adipic acid from crude oil is susceptible to problems such as the instability of oil price, the use of benzene which is a toxic material, the occurrence of environmental pollution by-products and the like. Moreover, recently, due to rising oil price, the price of chemical intermediate materials are rising, e.g., the material which is highly risen is butadiene which is the raw material of petroleum-based ABS (acrylonitrile-butadiene-styrene resin) and adipic acid which is to be the raw material of Nylon 66 resin. That is, the adipic acid is prepared via the intermediate cyclohexane, and the price of the cyclohexane consistently is rising.

Accordingly, if the production technology of nylon raw material having high availability, for example, is changed to a biomass based process, economic benefits would be expected and substantial effects can be expected in terms of an environmental aspect due to the reduction of environmental pollution.

However, the manufacturing process technology using biomass as a raw material is not established, and moreover, the bio-manufacturing process technology for synthesizing adipic acid which is a monomer of nylon 66 from biomass is just at the R&D level so far, it is not commercialized.

Thus, the development of a new bio-synthesis technology capable of manufacturing adipic acid at a low cost is urgently required.

On the other hand, as the currently known bio-technology, a producing method derived from green algae is disclosed in Korean patent application No. 10-2011-0073628. The method relates to a method for manufacturing D-glucaric acid by using green algae sugars, and more particularly a method for changing D-glucuronic acid obtained from a green algae primitive to D-glucaric acid by using the recombinant microorganism introducing the glucaric acid production gene. However, although this method has the characteristics which is a new fermentation process for manufacturing a chemical having a high industrial value by using the green algae resources, it is not used industrially because the manufacturing process is complicated, e.g., it is performed by a diastatic technique involving preparing a monosaccharide from green algae primitive and the subsequent monosaccharide engineering step for manufacturing glucaric acid using the recombinant microorganism.

Further, Moon, T. S. et al. (2009) Appl. Environ. Microbiol. 75:589-595 disclose the example which produces biomass-derived D-glucaric acid by using D-glucose as a raw material. However, the existing study producing glucaric acid by using D-glucose has the disadvantage of which the productivity is very low as compared with the injected glucose amount, because D-glucaric acid is produced through the chain enzyme reaction such as PPS (phosphoenolpyruvate-dependent phosphotransferase system), myo-inositol-1-phosphate synthase, phosphatase, myo-inositol oxygenase, myo-inositol oxygenase, etc. in Colon *bacillus* (<17.4%)

SUMMARY OF THE DISCLOSURE

In order to address the above problems, the present inventors have studied glucaric acid synthesis methods, and as a result, have found that glucaric acid, which is an intermediate used to produce adipic acid and which is one of raw materials of nylon used in large quantities industrially, can be manufactured through a chemical reaction from an aldohexose obtained from plant or marine resources.

Concretely, a method for producing glucaric acid according to the present disclosure comprises the steps of:

(1) inputting aldohexose and potassium hydroxide to an aqueous solution; and (2) deriving a catalytic oxidation reaction after adding a supported noble metal catalyst to the aqueous solution under a presence of oxygen gas.

Also, according to the present disclosure, glucaric acid is provided which has a particle form of the mono salt of potassium (K+) to an end and which has a melting point of 188° C. The glucaric acid potassium salt can be the raw material of adipic acid.

Hereinafter, a method for producing glucaric acid according to the present disclosure will be described in detail with reference to the specific examples. At this time, the following description is not limited to particular embodiments of the present disclosure, it must be understood as including all of changes, equivalents, and substitutes included in the spirit and scope of the present disclosure. Also, various components used in the following detailed description are not limited to the described terms. In addition, the terms used to the detailed description, including technical terms and scientific terms, has the same meaning as commonly understood by those of ordinary skill in the art unless otherwise defined.

The present disclosure provides a novel synthesis method for producing adipic acid at low cost in order to address the above problems. That is, we determine that it is possible to manufacture bio-adipic acid by a reduction reaction from glucaric acid through the study for synthesizing bio-adipic acid (biomass→glucaric acid→adipic acid). For this, a method according to the present disclosure provides a method capable of synthesizing glucaric acid by a simple process introducing an oxidation reaction, at the same time it utilizes aldohexose obtained from plants or marine resources. In particular, by easily synthesizing glucaric acid in under mild process conditions, that is, in a low temperature condition, it has an economic advantage as compared to methods using known microbial metabolic engineering. For reference, the United States Department of Energy has selected glucaric acid as one of the top 10 value added chemicals from biomass (US Department of Energy (2004) Top Value Added Chemicals from Biomass).

A method for producing glucaric acid according to an embodiment of the present disclosure comprises the steps of:
(1) inputting aldohexose and potassium hydroxide to an aqueous solution; and
(2) deriving a catalytic oxidation reaction after adding a supported noble metal catalyst to the aqueous solution under a presence of oxygen gas.

In the method of the present disclosure, it is preferred to use an aqueous solution of the reaction solvent. This is because the solubility of the aqueous solution is high for monosaccharides such as aldohexose and potassium hydroxide, and at the same time, it has the advantage which is much eco-friendly compared to the common organic solvents including alcohols.

Subsequently, aldohexose and potassium hydroxide is successively inputted to the reaction solvent.

At this time, aldohexose which is the starting material is a compound of hexose, it exists in hexagonal annular shape rather than chain shape generally. The method according to the present disclosure may use one of i) glucose and ii) galactose which are structural isomers.

It is preferable that the concentration of the aldohexose is about 0.01 g/cc to 0.2 g/cc, preferably, 0.02 g/cc to 0.2 g/cc to water which is the reaction solvent. If, the concentration is less than 0.01 g/cc, the concentration of the reactant is low, so the economy is decreased, and if the concentration is more than 0.2 g/cc, the contact area with oxygen and catalyst is small, so it has the disadvantage which the efficiency of the reaction drops.

Also, in the method of the present disclosure, the potassium hydroxide is the component which acts to hydrate aldohexose, and it is preferable that the mixture (mol) ratio of aldohexose:potassium hydroxide is 1:3 to 5 mol, preferably 1:3.5 to 4.5 mol. If the ratio is less than 1:3 mol, the reaction conversion rate decrease occurs, and if the ratio is more than 1:5 mol, it has the disadvantage which the economy is decreased.

Then, in the method of the present disclosure, a supported noble metal catalyst is added under the condition that the oxygen gas is flowed to the reactor.

At this time, the oxygen gas is a reaction gas to induce the catalytic oxidation reaction, and it is preferable to proceed while it is flowed so that the pressure in the reactor is at a level of 1 to 2.0 bars. If the pressure in the reactor is less than 1 bar, the reaction time may be increased, and if the pressure in the reactor is more than 2.0 bars, it has the disadvantage which a side reaction is not generated.

Also, a supported noble metal catalyst is the catalyst to induce the oxidation reaction of aldohexose, it is the metal element supported in at least one kind of supporting material selected from the group consisting of activated carbon (carbon), silica ($SiO_2$) and alumina ($Al_2O_3$). At this time, platinum is can be used as an example of the metal element, and besides, at least one of kind of rhodium, palladium and nickel can be selectively used. It is preferable that the supported noble metal catalyst of the present disclosure includes a carbon-supported platinum catalyst or an alumina supported platinum catalyst.

Further, in the method of the present disclosure, the supported noble metal catalyst may be included to the extent of 30 weight % to 50 weight % based on the aldohexose total content. If the content of the catalyst is less than 30 weight, the reactant concentration is low, so the economic is decreased, and if the content of the catalyst is more than 50 weight %, it has the disadvantages which are uneconomical effect depending on over-use of the catalyst and the side reaction due to excessive oxidation may be occurred. The present reaction condition is the condition which the reaction proceeds in the aqueous solution in low temperature, and if the content of the catalyst is less than 30 weight %, the oxidation reactivity is lowered, and if the content of the catalyst exceeds 50 weight %, a side reaction is occurred.

By the catalyst oxidation reaction, aldohexose, for example, glucose may be changed into the form of a glucaric acid potassium salt, or galactose may be changed into the form of a galactaric acid or taric acid potassium salt (see the following reaction formula 1)

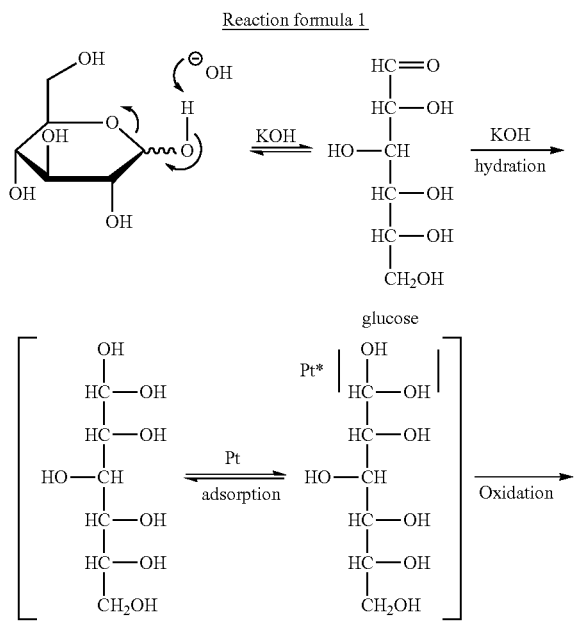

Reaction formula 1

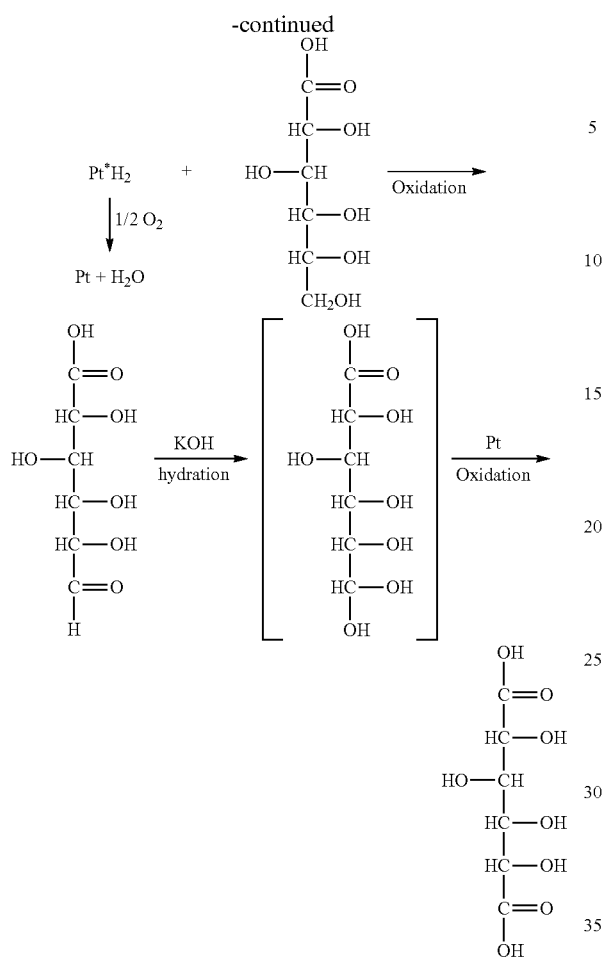

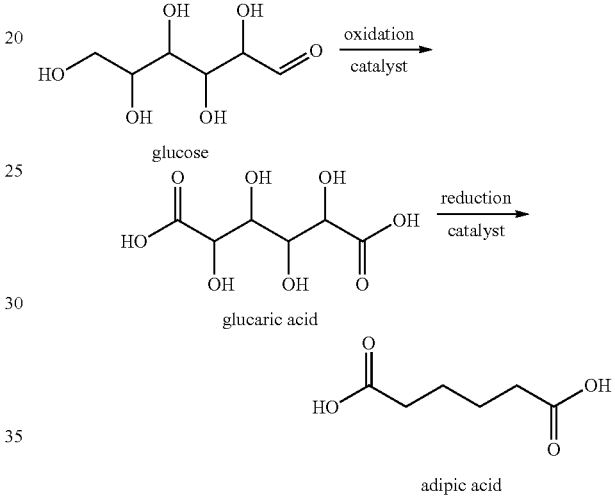

glucose glucaric acid adipic acid

That is, in the case of glucose in aqueous solution, the equilibrium is inclined to a cyclic form known as a stable structure as compared with a linear form, and at this time, the salt (basic) condition functions as assistant so that the equilibrium is moved to the linear form a little more, and at the same time, by hydration reacting with aldehyde of the end, the efficiency of the oxidation is increased.

At this time, glucaric acid or galactaric acid are carboxylic acids, they exist in different form according to pH as follows (see reaction formula 2)

range (pH 3 to 4), glucaric acid or galactaric acid gives only one hydrogen cation ($H^+$) and the form which only one side is base can be obtained.

At this time, the catalyst oxidation reaction can be carried under the conditions of about 30° C. to 60° C. temperature, preferably raised to about 50° C. level. For example, in order to efficiently pass the reaction by accelerating the oxidation reaction, since a certain amount of energy is required, heat is applied. However, if the reaction is performed in high temperature of more than 60° C., a side reaction may occur due to excessive oxidation. Hence, a proper temperature level is preferred, and the most optimized temperature is about 50° C.

In this respect, glucaric acid can be produced from glucose by the chemical synthesis reaction of aldohexose, for example, glucose which is soluble in aqueous solution, and the catalyst. (See Reaction formula 3).

The glucaric acid has a particle shape of a mono salt form which potassium (K) is combined to an end, and the melting point is 188° C.

Further, the produced glucaric acid is an eco-friendly chemical intermediate new material which can be produced at low cost, and can have the characteristic capable of manufacturing adipic acid which is a raw material of Nylon 66 through an additional chemical reaction at a low cost. Further, the glucaric acid is used as a manufacturing raw material of Reaction formula 2

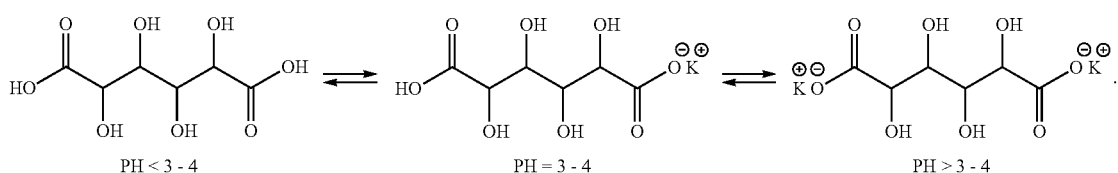

That is, the concepts of acid and base are relative concepts, and in the condition which is more basic than carboxyl, carboxyl acts as acid, loses hydrogen cation ($H^+$) and exists as a form of a salt with potassium cation ($K^+$), and if it is changed in the condition which is more acid, the salt acts as the base, receives hydrogen cation ($H^+$) and exists in a form of carboxylic acid. In the same context, if the pH is adjusted to pH bio-adipic acid which is monomer, and biomass-derived bio Nylon 66 used as an automotive engine chassis injection part can be manufactured at a low cost.

According to the method of the present disclosure, since glucaric acid which is an intermediate in the manufacturing of Nylon 66 which itself is used as a material for parts for vehicles can be easily synthesized at a low temperature condition and a low pressure process condition, the industrial availability is very high. Also, the manufacturing method is easier than the existing known methods using a microorganism, and ultimately, the biomaterial can be manufactured at low cost, so it is economical.

BRIEF DESCRIPTION OF THE DRAWINGS

The above and other objects, features and advantages of the present disclosure will be more apparent from the following detailed description taken in conjunction with the accompanying drawings, in which.

DETAILED DESCRIPTION OF THE PREFERRED EMBODIMENTS

Hereinafter, a method for producing glucaric acid according to the present disclosure will be described in detail with reference to the following embodiments. At this time, the specific embodiments of the present disclosure are not intended to limit the present disclosure, and it shall be understood to include all of the changes, equivalents and substitutes included in the spirit and scope of the present disclosure.

EMBODIMENT

Embodiment 1

Depending on the ratio shown in Table 1, as a starting material, glucose is inputted into the reactor at 0.1 g/cc concentration to aqueous solvent, and then potassium hydroxide is inputted at 1:3 mol ratio to glucose. Then, a platinum catalyst supported on activated carbon was added to the 30 weight % extent to the glucose. Then, the temperature of the reactor is maintained to 50° C., and it was reacted during 4 hours while inputting oxygen gas into the reactor and maintaining the pressure at a 1 bar level.

Figure 1:
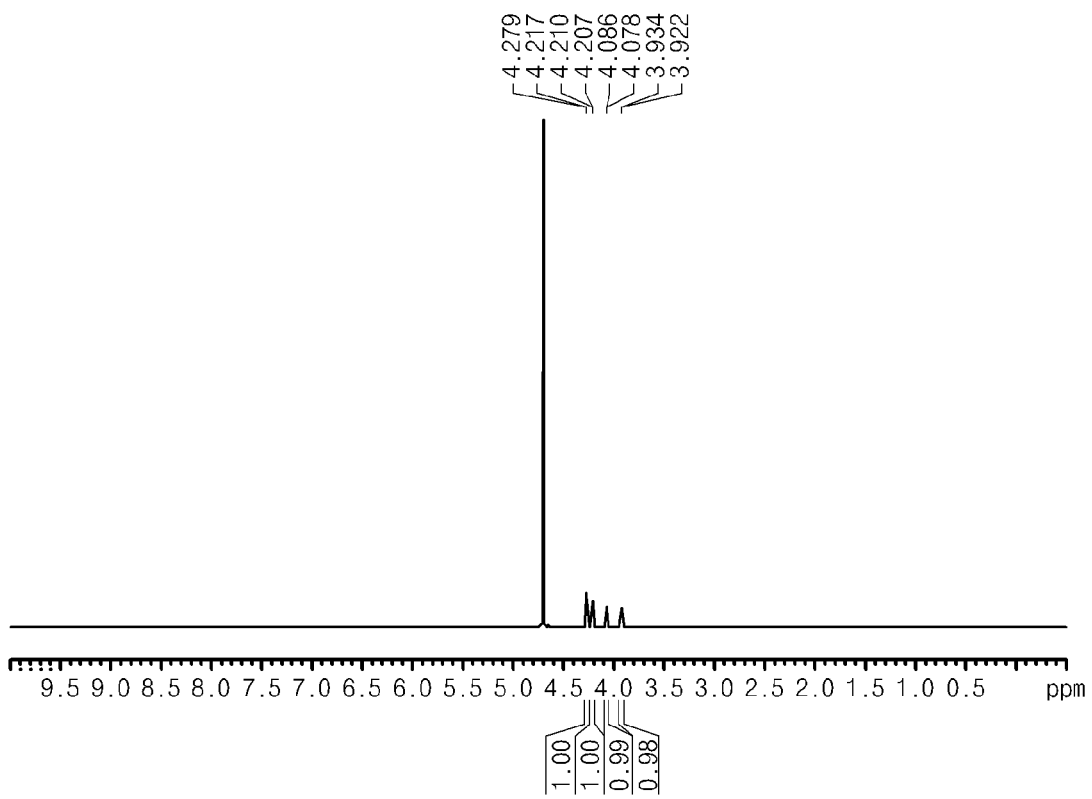
FIG. 1 is $^1$H NMR data of glucaric acid manufactured according to Embodiment 1 of the present disclosure.

At the end of the reaction, it was confirmed that glucaric acid was synthesized by performing nuclear magnetic resonance analysis (Bruker AVIII400 Instrument) and FT IR instrument analysis (Agilent Technologies Cary 600), after separating water from reactant (see FIG. 1). At this time, NMR spectrum was performed by dissolving the sample in $D_2O$ including TMS (trimethylsilane) as an internal standard ($^1$H at 400 MHz).

$^1$H NMR δ 4.14 (d, J=3.2, 1H),
4.09 (d, J=4.4, 1H),
3.96 (dd, J=3.2, 2.0, 1H),
3.80 (apparently t, J=5.0).
FT-IR (equipped with ATR accessory) 3252, 1742 cm$^{-1}$

Embodiment 2

Depending on the ratio shown in Table 1, as a starting material, glucose is inputted into the reactor at 0.1 g/cc concentration to aqueous solvent, and then potassium hydroxide is inputted at 1:4 mol ratio to glucose. Then, a platinum catalyst supported on activated carbon was added to the 50 weight % extent to the glucose. Then, the temperature of the reactor is maintained to 50° C., and it was reacted during 4 hours while inputting oxygen gas into the reactor and maintaining the pressure at a 1.5 bar level.

Figure 2:
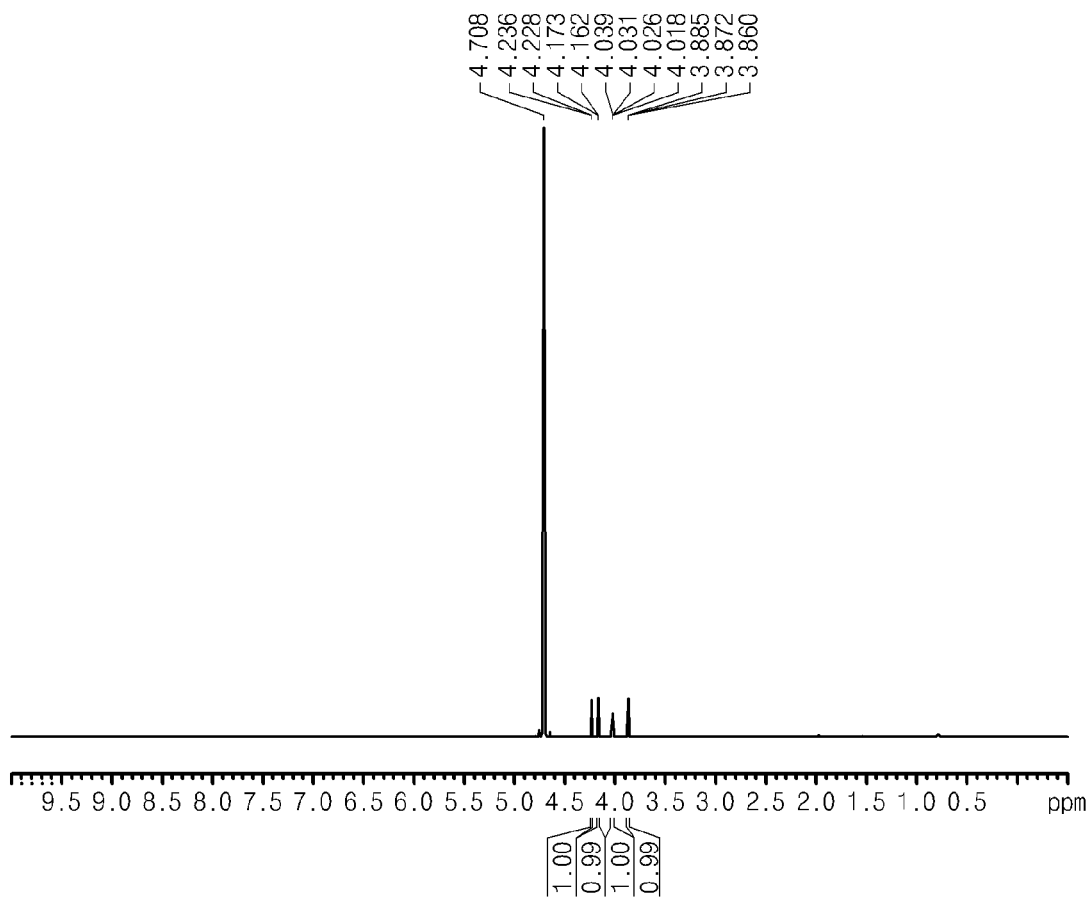
FIG. 2 is $^1$H NMR data of glucaric acid manufactured according to Embodiment 2 of the present disclosure.
Figure 3:
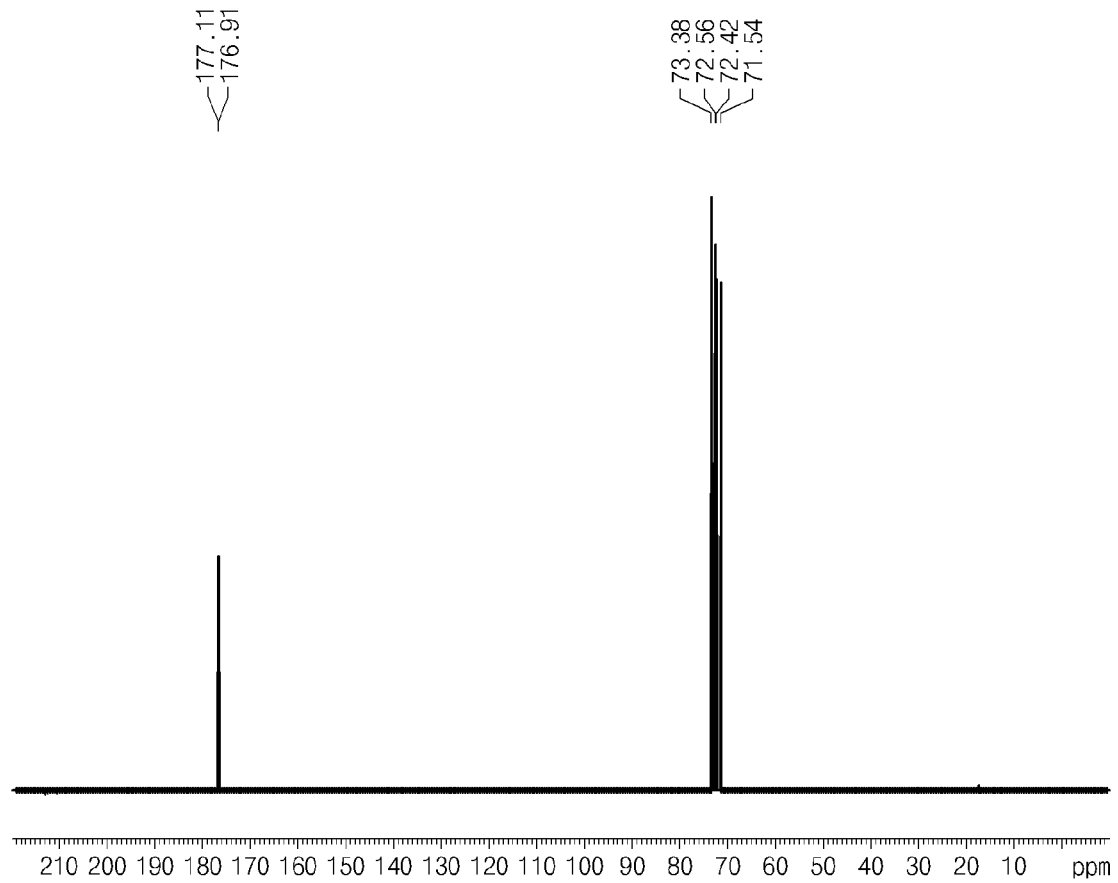
FIG. 3 is $^{13}$H NMR data of glucaric acid manufactured according to Embodiment 2 of the present disclosure.

At the end of the reaction, it was confirmed that glucaric acid was synthesized by performing nuclear magnetic resonance analysis (Bruker AVIII400 Instrument) and FT IR instrument analysis (Agilent Technologies Cary 600), after separating water from reactant (see FIG. 2 and FIG. 3) ($^1$H at 400 MHz, $^{13}$C at 100 MHz).

$^1$H NMR δ 4.14 (d, J=3.2, 1H),
4.09 (d, J=4.4, 1H),
3.96 (dd, J=3.2, 2.0, 1H),
3.80 (apparently t, J=5.0).
$^{13}$C NMR δ 177.1, 176.9, 73.4, 72.6, 72.4, 71.5
FT-IR (equipped with ATR accessory) 3252, 1742 cm$^{-1}$

Embodiment 3

Depending on the ratio shown in Table 1, as a starting material, glucose is inputted into the reactor at 0.1 g/cc concentration to aqueous solvent, and then potassium hydroxide is inputted at 1:5 mol ratio to glucose. Then, a platinum catalyst supported on activated carbon was added to the 40 weight % extent to the glucose. Then, the temperature of the reactor is maintained to 50° C., and it was reacted during 4 hours while inputting oxygen gas into the reactor and maintaining the pressure at a 2 bar level.

Figure 4:
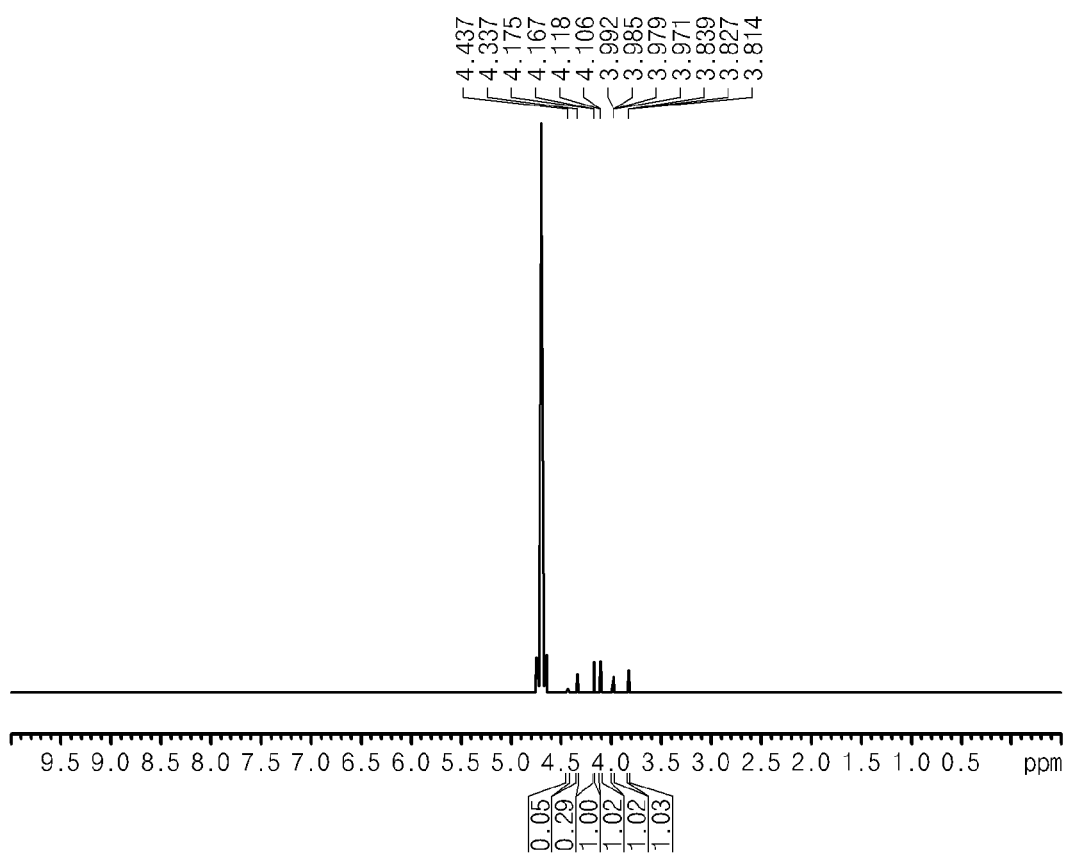
FIG. 4 is $^1$H NMR data of glucaric acid manufactured according to Embodiment 3 of the present disclosure.

At the end of the reaction, it was confirmed that glucaric acid was synthesized by performing nuclear magnetic resonance analysis (Bruker AVIII400 Instrument) and FT IR instrument analysis (Agilent Technologies Cary 600), after separating water from reactant (see FIG. 4)

$^1$H NMR δ 4.14 (d, J=3.2, 1H),
4.09 (d, J=4.4, 1H),
3.96 (dd, J=3.2, 2.0, 1H),
3.80 (apparently t, J=5.0).
FT-IR (equipped with ATR accessory) 3252, 1742 cm$^-$

Embodiment 4

Depending on the ratio shown in Table 1, as a starting material, glucose is inputted into the reactor at 0.1 g/cc concentration to aqueous solvent, and then potassium hydroxide is inputted at 1:4 mol ratio to glucose. Then, a platinum catalyst supported on activated carbon was inputted to the 30 weight % extent to the glucose. Then, the temperature of the reactor is maintained to 50° C., and it was reacted during 4 hours while inputting oxygen gas into the reactor and maintaining the pressure at a 1.5 bar level.

Figure 5:
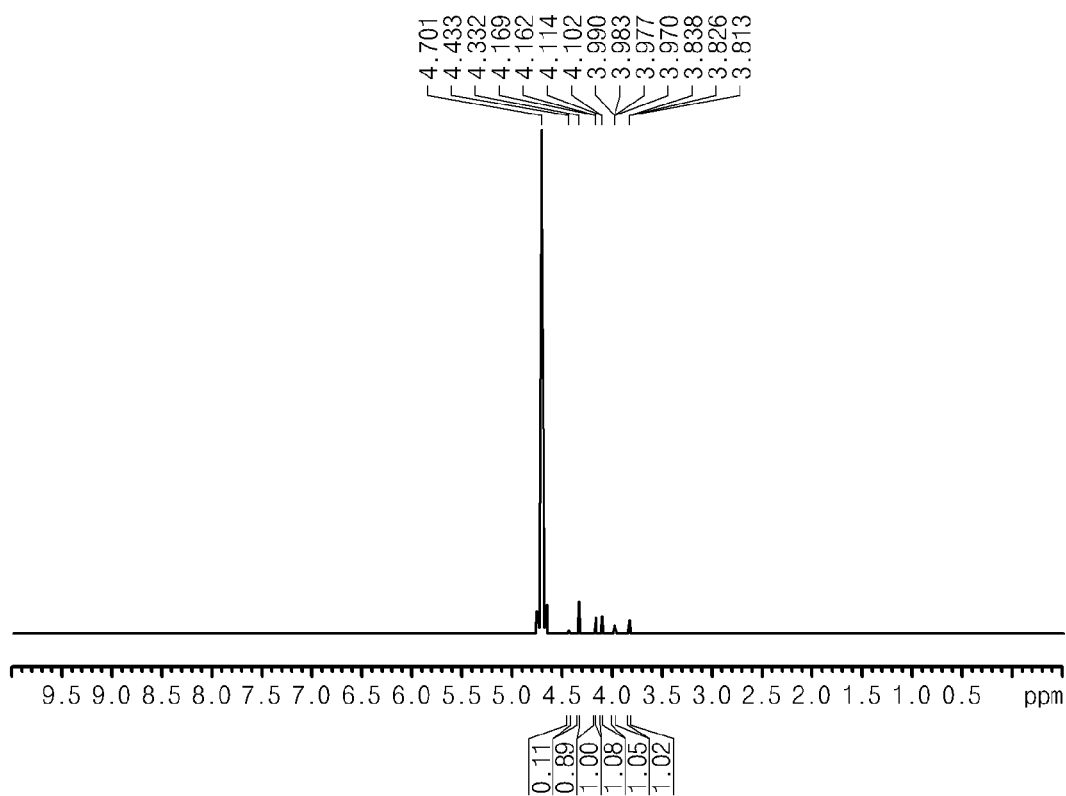
FIG. 5 is $^1$H NMR data of glucaric acid manufactured according to Embodiment 4 of the present disclosure.

At the end of the reaction, it was confirmed that glucaric acid was synthesized by performing nuclear magnetic resonance analysis (Bruker AVIII400 Instrument) and FT IR instrument analysis (Agilent Technologies Cary 600), after separating water from reactant (see FIG. 5)

$^1$H NMR δ 4.14 (d, J=3.2, 1H),
4.09 (d, J=4.4, 1H),
3.96 (dd, J=3.2, 2.0, 1H),
3.80 (apparently t, J=5.0).
FT-IR (equipped with ATR accessory) 3252, 1742 cm$^-$

Comparative Example 1

Figure 6:
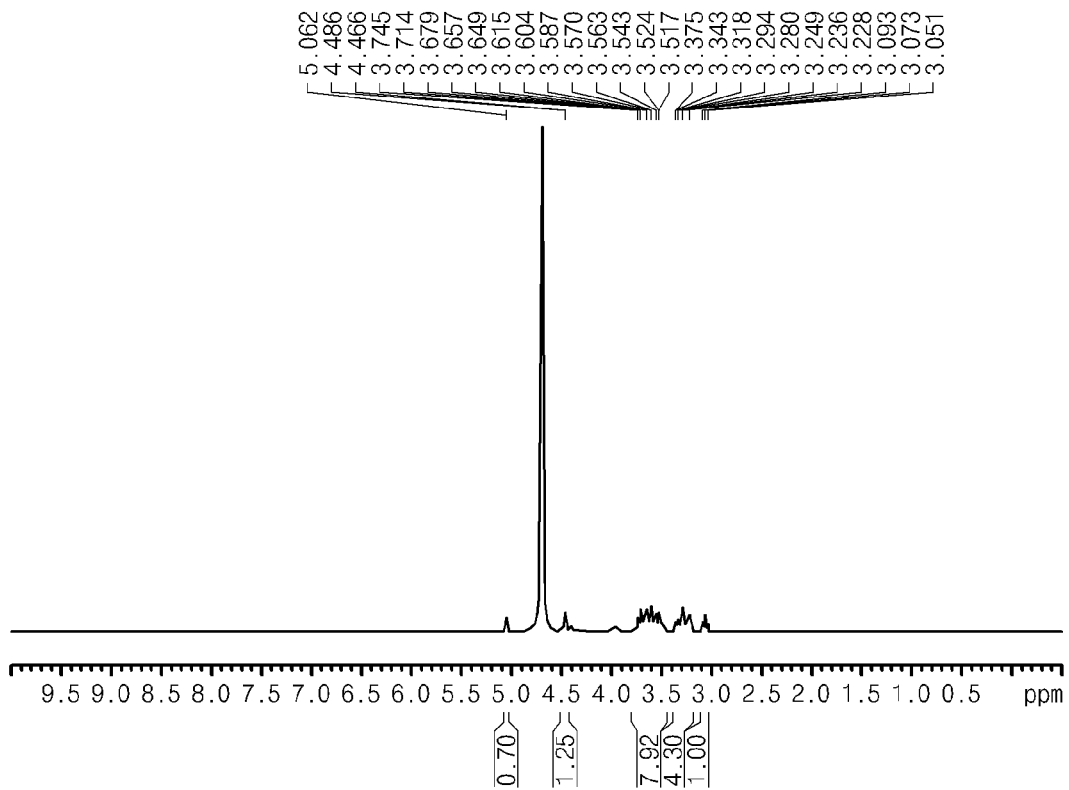
FIG. 6 is $^1$H NMR data of a product obtained in Comparative example 1.

Depending on the ratio shown in Table 1, as a starting material, glucose is inputted into the reactor at 0.1 g/cc concentration to aqueous solvent, and then a platinum catalyst supported on activated carbon was added to the 10 weight % extent to the glucose. Then, oxygen gas was inputted into the reactor and the pressure was maintained to a 1 bar level while maintaining temperature of the reactor to room temperature (25° C.). After the reaction time of 8 hours, if the reaction is finished, it was determined that glucaric acid was produced by analyzing the component of the product, after separating water from reactant. That is, as the result of NMR analysis, in Comparative example 1 outside the specified reaction condition range disclosed in the present disclosure, it can be seen that glucaric acid was not well synthesized (see FIG. 6).

Comparative Example 2

Figure 7:
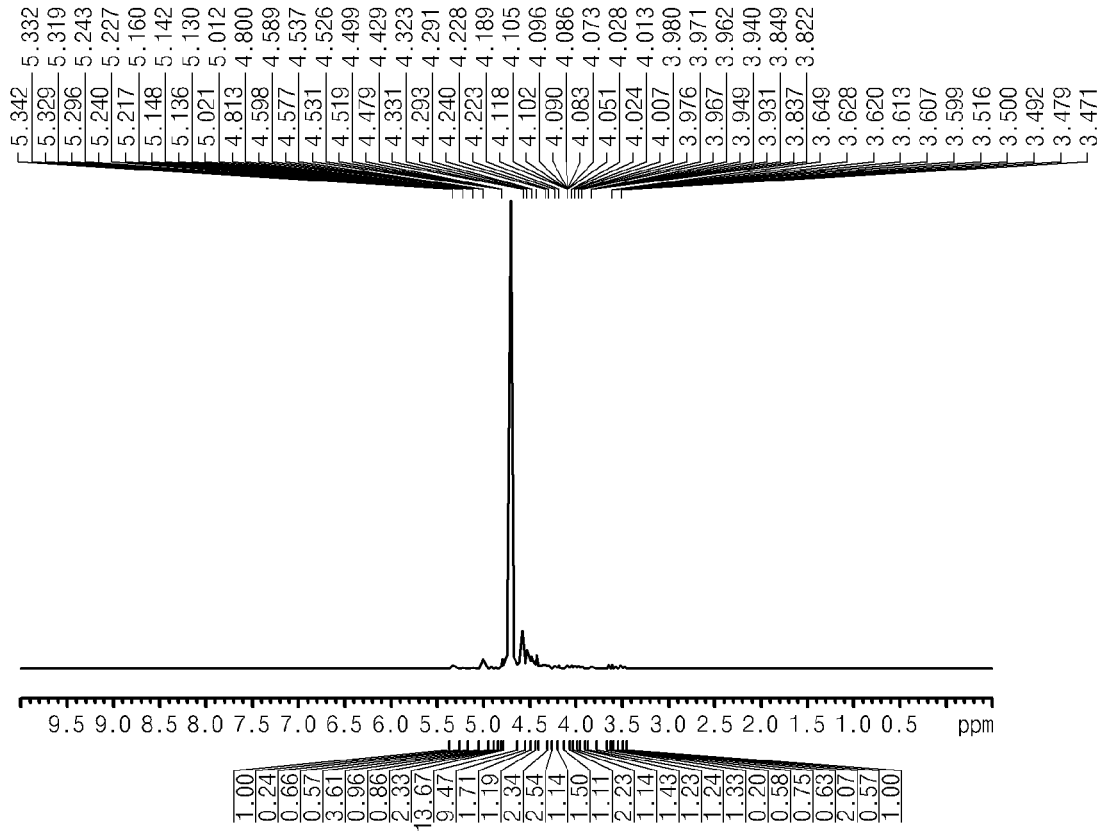
FIG. 7 is $^1$H NMR data of a product obtained in Comparative example 2.

Depending on the ratio shown in Table 1, as a starting material, glucose is inputted into the reactor at 0.1 g/cc concentration to aqueous solvent, and then a platinum catalyst supported on activated carbon was added to the 40 weight % extent to the glucose. Then, oxygen gas was inputted into the reactor and the pressure was maintained to a 5 bar level while maintaining temperature of the reactor to 80° C. After the reaction time of 8 hours, if the reaction is finished, it was determined that glucaric acid was produced by analyzing the component of the product, after separating water from reactant. That is, as the result of NMR analysis, in Comparative example 2 outside the specified reaction condition range disclosed in the present disclosure, it can be seen that glucaric acid was not well synthesized (see FIG. 7).

Comparative Example 3

Figure 8:
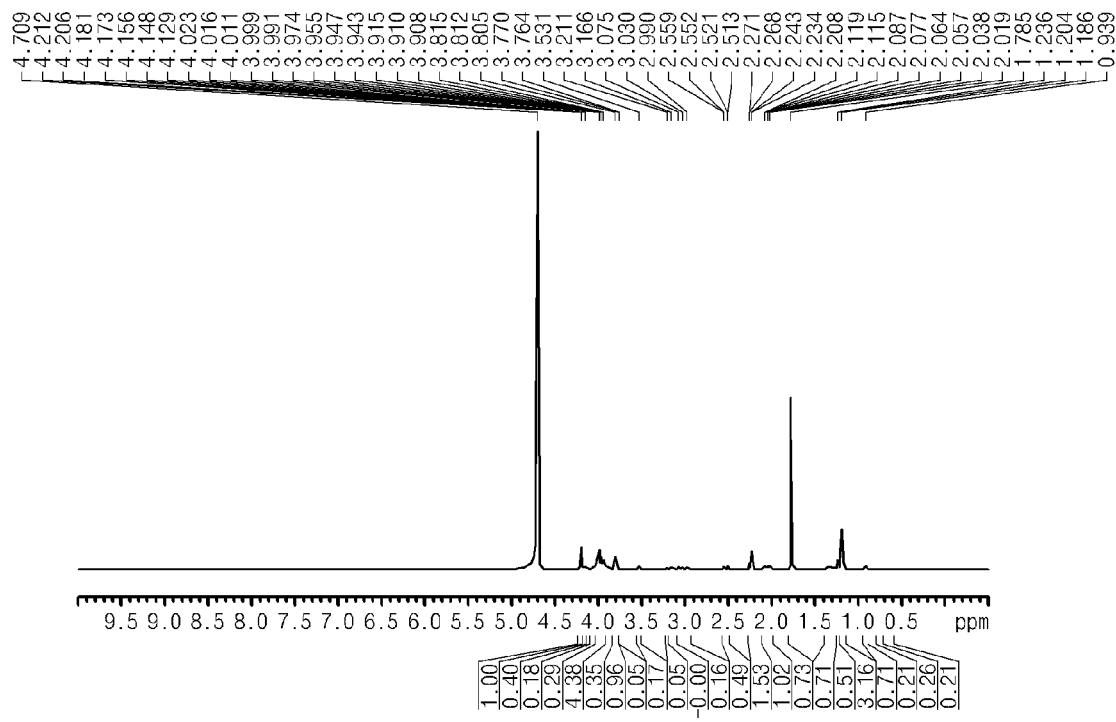
FIG. 8 is $^1$H NMR data of a product obtained in Comparative example 3.

Depending on the ratio shown in Table 1, as a starting material, glucose is inputted into the reactor at 0.1 g/cc concentration to aqueous solvent, and then potassium hydroxide is inputted at 1:3 mol ratio to glucose. Then, a platinum catalyst supported on activated carbon was added to the 15 weight % extent to the glucose. Then, oxygen gas was inputted into the reactor and the pressure was maintained to 5.0 bar level while maintaining temperature of the reactor to 80° C. After the reaction time of 4 hours, if the reaction is finished, it was determined that glucaric acid was produced by analyzing the component of the product, after separating water from reactant. That is, as the result of NMR analysis, in Comparative example 3 outside the specified reaction condition range disclosed in the present disclosure, it can be seen that glucaric acid was not well synthesized (see FIG. 8).

Comparative Example 4

Figure 9:
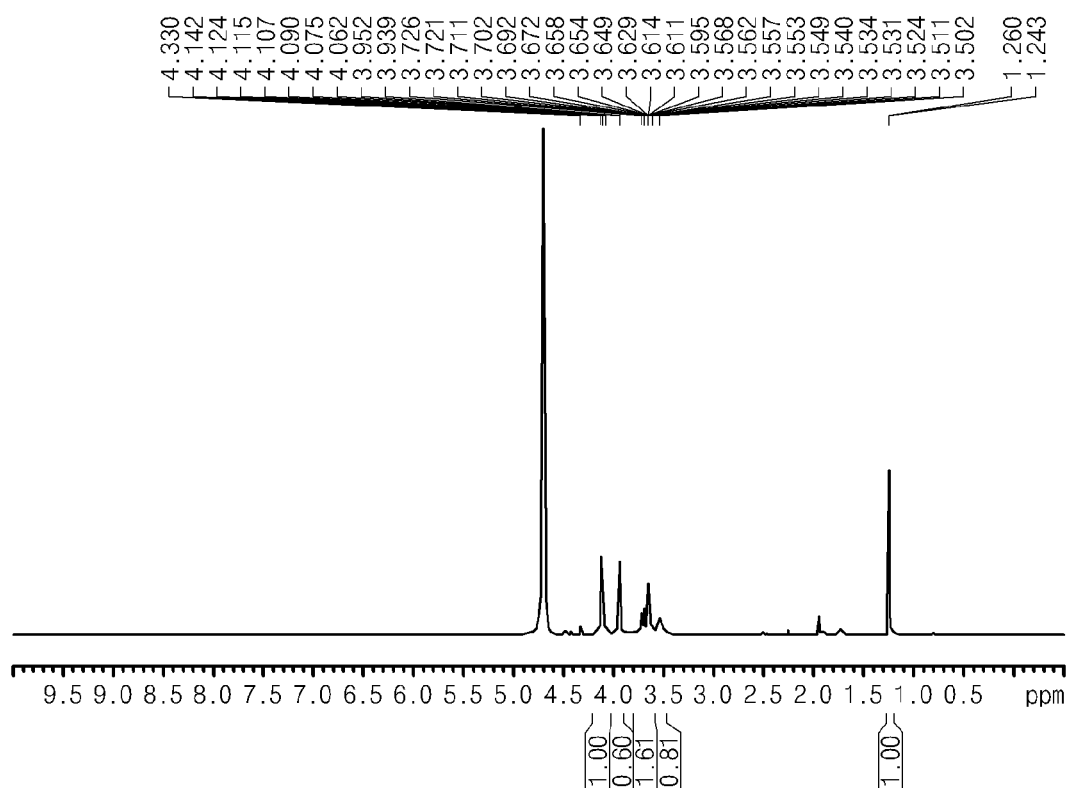
FIG. 9 is $^1$H NMR data of a product obtained in Comparative example 4.

Depending on the ratio shown in Table 1, as a starting material, glucose is inputted into the reactor at 0.1 g/cc concentration to aqueous solvent, and then a platinum catalyst supported on activated carbon was added to the 50 weight % extent to the glucose. Then, oxygen gas was inputted into the reactor and the pressure was maintained to 10 bar level while maintaining temperature of the reactor to 50° C. After the reaction time of 4 hours, if the reaction is finished, it was determined that glucaric acid was produced by analyzing the component of the product, after separating water from reactant. That is, as the result of NMR analysis, in Comparative example 4 outside the specified reaction condition range disclosed in the present disclosure, it can be seen that glucaric acid was not well synthesized (see FIG. 9).

|  | Example | | | | Comparative Example | | | |
| --- | --- | --- | --- | --- | --- | --- | --- | --- |
|  | 1 | 2 | 3 | 4 | 1 | 2 | 3 | 4 |
| (A) | 0.1 g/cc | | | | 0.1 g/cc | | | |
| (B) | 1:3 | 1:4 | 1:5 | 1:4 | — | — | 1:3 | 1:4 |
| (C) | 30 wt % | 50 wt % | 40 wt % | — | 10 wt % | 40 wt % | 15 wt % | 50 wt % |
| (D) | — | — | — | 50 wt % | — | — | — | — |
| reaction temperature | 50° C. | 50° C. | 50° C. | 50° C. | 25° C. | 80° C. | 80° C. | 50° C. |
| reaction pressure | 1.0 bar | 1.5 bar | 2.0 bar | 1.5 bar | 1.0 bar | 5.0 bar | 5.0 bar | 10 bar |
| whether glucaric acid is synthesized | ○ | ○ | ○ | ○ | X | X | X | X |

(A): glucose(Glucose Monohydrate(product name); Korea Daesang(co.):water ratio
(B): glucose(Glucose Monohydrate(product name); Korea Daesang(co.):potassium hydroxide (America sigma Aldrich(Co.)) mol ratio
(C): carbon-supported platinum catalyst (America sigma Aldrich(Co.))
(D): alumina supported platinum catalyst (America sigma Aldrich(Co.))

What is claimed is:

1. A method for producing glucaric acid having a particle form of a mono salt comprising the steps of:
   inputting aldohexose and potassium hydroxide to an aqueous solution; and
   deriving a catalytic oxidation reaction within a pH range of 3 to 4 after adding a supported noble metal catalyst to the aqueous solution under a presence of oxygen gas,
   wherein a mixture (mole) ratio of the aldohexose to potassium hydroxide (aldohexose:potassium hydroxide) is 1:3.0 to 1:5.0 moles, and
   the supported noble metal catalyst is added to the aqueous solution at 30 weight % to 50 weight % based on an aldohexose total content.

2. A method for producing glucaric acid according to claim 1, wherein the aldohexose is glucose or galactose.

3. A method for producing glucaric acid according to claim 1, wherein the aldohexose is imputed at a concentration of 0.02 g/cc to 0.2 g/cc to the aqueous solution.

4. A method for producing glucaric acid according to claim 1, wherein the oxygen gas is inputted so that a pressure in a reactor is maintained at 1 to 2.0 bars.

5. A method for producing glucaric acid according to claim 1, wherein the supported noble metal catalyst includes a metal element supported in at least one supporting material selected from the group consisting of activated carbon (carbon), silica ($SiO_2$) and alumina ($Al_2O_3$).

6. A method for producing glucaric acid according to claim 5, wherein the metal element is one selected from the group consisting of platinum, rhodium, palladium and nickel.

7. A method for producing glucaric acid according to claim 1, wherein the supported noble metal catalyst is a carbon-supported platinum catalyst or an alumina supported platinum catalyst.

8. A method for producing glucaric acid according to claim 1, wherein the catalyst oxidation reaction is performed under a 30° C. to 60° C. temperature condition.

* * * * *